(12) United States Patent
Cazeneuve et al.

(10) Patent No.: US 10,604,394 B1
(45) Date of Patent: Mar. 31, 2020

(54) CARTRIDGE AND A BASE UNIT FOR USE IN AN ORAL CARE APPLIANCE

(71) Applicant: Willo 32 SAS, Limoges (FR)

(72) Inventors: Pierre Jules Hercule Cazeneuve, Saint-Cloud (FR); Jean-Raphaël Ouin, Paris (FR)

(73) Assignee: Willo 32 SAS, Limoges (FR)

( * ) Notice: Subject to any disclaimer, the term of this patent is extended or adjusted under 35 U.S.C. 154(b) by 0 days.

(21) Appl. No.: 16/270,370

(22) Filed: Feb. 7, 2019

(51) Int. Cl.
*B67B 7/20* (2006.01)
*B67B 7/86* (2006.01)
*A61C 17/00* (2006.01)

(52) U.S. Cl.
CPC ............... *B67B 7/28* (2013.01); *A61C 17/00* (2013.01)

(58) Field of Classification Search
CPC .................................. B67B 7/28; A61C 17/00
USPC .................................. 141/285, 302, 319, 330
See application file for complete search history.

(56) References Cited

U.S. PATENT DOCUMENTS

| | | | | |
|---|---|---|---|---|
| 3,256,894 A | * | 6/1966 | Sherman | A46B 11/0055 222/209 |
| 3,400,996 A | * | 9/1968 | Vandergrift | A46B 11/0055 401/143 |
| 4,049,354 A | * | 9/1977 | O'Rourke | A46B 11/0041 401/134 |
| 6,003,702 A | * | 12/1999 | Grimard | A61J 1/2089 141/24 |
| 6,206,058 B1 | * | 3/2001 | Nagel | A47L 13/20 141/302 |
| 6,406,207 B1 | * | 6/2002 | Wiegner | A46B 11/0027 401/272 |
| 6,547,106 B2 | * | 4/2003 | Bonningue | B05B 11/3028 137/512 |
| 7,082,638 B2 | | 8/2006 | Koh | |
| 7,086,431 B2 | * | 8/2006 | D'Antonio | B65B 3/003 141/285 |
| 7,537,451 B1 | | 5/2009 | Ramnarine | |
| 7,789,583 B2 | * | 9/2010 | Kuo | A46B 11/0058 401/188 R |
| 8,448,282 B2 | | 5/2013 | Stapelbroek | |
| 8,534,500 B2 | * | 9/2013 | Baier | A61C 17/227 222/94 |
| 8,596,310 B2 | * | 12/2013 | Senno | B29C 73/166 141/105 |
| 8,617,090 B2 | | 12/2013 | Fougere | |
| 8,635,731 B2 | | 1/2014 | Garner | |
| 8,667,634 B2 | | 3/2014 | Steur | |
| 8,667,996 B2 | * | 3/2014 | Gonnelli | A61J 1/2089 141/322 |
| 8,745,802 B2 | | 6/2014 | Steur | |
| 8,863,346 B2 | | 10/2014 | Headstrom | |

(Continued)

FOREIGN PATENT DOCUMENTS

EP 2654609 B1 3/2018
EP 2654611 B1 4/2018

(Continued)

*Primary Examiner* — Timothy L Maust
(74) *Attorney, Agent, or Firm* — Daylight Law, P.C.

(57) ABSTRACT

A cartridge and a base unit for use in an oral care appliance are disclosed. The cartridge includes a connection interface configured to form a detachable connection. The base unit is also configured to engage operatively with the cartridge to facilitate flow of an oral care composition from the cartridge into the oral care appliance.

19 Claims, 9 Drawing Sheets

(56) References Cited

U.S. PATENT DOCUMENTS

| | | |
|---|---|---|
| 8,978,189 B1 | 3/2015 | Sexton |
| 8,990,992 B2 | 3/2015 | Stapelbroek |
| 9,084,655 B2 | 7/2015 | Sahoo |
| 9,277,980 B2 | 3/2016 | Leveling |
| 9,308,065 B2 | 4/2016 | Steiner |
| 9,504,542 B2 | 11/2016 | De Gentile |
| 9,526,597 B2 | 12/2016 | Steur |
| 9,636,195 B2 | 5/2017 | Wolpo |
| 9,636,197 B2 | 5/2017 | Khangura |
| 9,668,840 B2 | 6/2017 | Miller |
| 9,907,633 B2 | 3/2018 | Wolpo |
| 2007/0184404 A1 | 8/2007 | Johnki |
| 2009/0119859 A1* | 5/2009 | Podolsky .............. A46B 11/002 15/167.1 |
| 2012/0301209 A1* | 11/2012 | Fattori ............... A46B 11/0041 401/171 |
| 2016/0113745 A1 | 4/2016 | Golub |
| 2016/0135581 A1 | 5/2016 | Pai |
| 2016/0206415 A1 | 7/2016 | Kraft |
| 2016/0270892 A1 | 9/2016 | Yoo |
| 2017/0367801 A1 | 12/2017 | Fitzgerald |
| 2018/0000573 A1 | 1/2018 | Miller |
| 2018/0184795 A1 | 7/2018 | Pai |
| 2018/0184857 A1 | 7/2018 | Pai |

FOREIGN PATENT DOCUMENTS

| | | |
|---|---|---|
| WO | 2017061980 A1 | 4/2017 |
| WO | 2017146366 A1 | 8/2017 |
| WO | 2018160986 A1 | 9/2018 |

* cited by examiner

CARTRIDGE AND A BASE UNIT FOR USE IN AN ORAL CARE APPLIANCE

BACKGROUND OF THE INVENTION

Dental cleaning devices such as electric toothbrushes, oral irrigators, dental water jets or electric flosses intend to provide cleaning results by eradicating the food remains, plaque, etc., from the teeth. Many of these devices are portable devices and have been developed over the years to achieve the purpose of oral hygiene.

In addition, along with the dental cleaning device, suitable dentifrice also plays an important role in oral hygiene. However, current brushing systems or dental cleaning devices that are meant to be used with dentifrice are usually not provided with integrated dentifrice dispensers. Thus, users must procure additional dentifrice dispensers if they want to achieve optimal oral care hygiene. This present situation is not ideal because current oral care appliances are not suitable for achieving by themselves optimal oral care hygiene.

SUMMARY OF THE INVENTION

A need exists for an oral care appliance that comprises an integrated dentifrice dispenser. Moreover, as different users may require different dentifrices, it is desirable to have oral care appliances with dentifrice dispensers which may be securely and easily engaged or disengaged with a handle or body portion of the oral care appliance.

Specific embodiments of the invention aim to address these needs by providing a cartridge and a base unit for use in an oral care appliance. The oral care appliance may be used for cleaning, whitening, removing plaque, and in other general oral care applications for providing oral care hygiene.

Specific embodiments of the invention include a cartridge for use in an oral care appliance. The cartridge comprises a housing for storing an oral care composition, a connection interface configured to form a detachable connection with the oral care appliance, and a valve assembly configured to prevent escape of the oral care composition when the connection interface is in a detached position and to allow flow of the oral care composition through the connection interface to the oral care appliance when the connection interface is in an attached position. The valve assembly is positioned in the connection interface and comprises at least two valves.

According to specific embodiments of the invention, the housing may have a symmetrical shape.

According to specific embodiments of the invention, at least a portion of the housing may be rigid.

According to specific embodiments of the invention, the housing of the cartridge may comprise a cavity for storing the oral care composition.

According to specific embodiments of the invention, the housing of the cartridge may comprise a flexible membrane configured to deform in response to pressure variations in the cartridge.

According to specific embodiments of the invention, the at least two valves of the valve assembly may be made of flexible material.

According to specific embodiments of the invention, the valve assembly may have only one valve wherein the valve is made of rigid material.

According to specific embodiments of the invention, the connection interface of the cartridge may be configured to interact with a base unit of the oral care appliance to allow the flow of oral care composition to the oral care appliance.

According to specific embodiments of the invention, the valve assembly may be configured to form at least one fluidic path allowing flow of the oral care composition through the connection interface to the oral care appliance.

According to specific embodiments of the invention, the connection interface may be a cartridge neck.

According to specific embodiments of the invention, the cartridge neck may be configured to facilitate easy and secure coupling of the cartridge to the base unit.

According to specific embodiments of the invention, the cartridge may further comprise an air intake aperture.

According to specific embodiments of the invention, the air aperture in the cartridge may be configured to regulate the pressure difference in the cartridge and the surrounding air.

According to specific embodiments of the invention, the symmetric shape of the housing may allow plugging of the cartridge to the base unit regardless of the direction of the cartridge.

Specific embodiments of the invention provide a base unit for use in an oral care appliance. The base unit comprises a connection interface to be plugged to a cartridge containing an oral care composition. The base unit comprises a needle assembly configured to be operatively engaged to the cartridge to facilitate flow of the oral care composition from the cartridge into the oral care appliance.

According to specific embodiments of the invention, the needle assembly of the base unit may comprise at least one aperture configured to allow the flow of oral care composition from the cartridge to the oral care appliance.

According to specific embodiments of the invention, the needle assembly of the base unit may comprise an additional aperture to facilitate the inlet of air to the cartridge.

According to specific embodiments of the invention, the additional aperture of the needle assembly may be configured to regulate the pressure inside the cartridge by facilitating the inlet of air to the cartridge during the extraction of the oral care composition.

According to specific embodiments of the invention, the needle assembly of the base unit may be configured to interact with the valve assembly positioned in the cartridge to form a sealed connection.

According to specific embodiments of the invention, the connection interface of the base unit may be configured to be coupled with the connection interface of the cartridge to make a sealed connection.

According to specific embodiments of the invention, the needle assembly of the base unit may be configured to form at least a fluidic path allowing flow of the oral care composition from the cartridge to the oral care appliance.

According to specific embodiments of the invention, the base unit may further comprise at least a first part made up of soft material configured to ensure a snug fit connection between the cartridge and the base unit.

According to specific embodiments of the invention, the base unit may further comprise at least a second part made up of hard material configured to provide support to the cartridge when it is plugged to the base unit.

According to specific embodiments of the invention, the length of the needle assembly may be dimensioned so that the needle is long enough to penetrate the valve assembly of the cartridge and short enough so that it allows for draining of the entire volume of oral care composition contained in the cartridge.

According to specific embodiments of the invention, the base unit may be configured to allow plugging and/or unplugging of the cartridge to the oral care appliance without any leakage of the oral care composition.

According to specific embodiments of the invention, the base unit may comprise means to form a snug fit connection with the cartridge.

According to specific embodiments of the invention, the means of the base unit may comprise at least a male connector or at least a female connector facilitating the connection between the base unit and the cartridge.

According to specific embodiments of the invention, the diameter of the female connector of the base unit may be smaller than the exterior diameter of the cartridge cap to allow for plugging and unplugging of the cartridge to the oral care appliance without any leak.

According to specific embodiments of the invention, the base unit may be shaped to match the cartridge shape.

According to specific embodiments of the invention, the base unit may comprise a mixing chamber to extract the oral care composition from the cartridge and to regulate the pressure inside the cartridge.

According to specific embodiments of the invention, the base unit may comprise a venturi effect chamber for aspiration/dispensing of the oral care composition from the cartridge.

Various objects, features, aspects and advantages of the present disclosure will become more apparent from the following detailed description of preferred embodiments, along with the accompanying drawing figures in which like numerals represent like features

DETAILED DESCRIPTION

Aspects of the present invention can be understood by reference to the figures and description set forth herein. However, the following descriptions, and numerous specific details thereof, are given by way of illustration and not of limitation. Many changes and modifications to the specific descriptions may be made without departing from the spirit and scope thereof, and the present invention includes all such modifications. It is to be understood that the disclosed embodiments may or may not overlap with each other. Thus, part of one embodiment, or specific embodiments thereof, may or may not fall within the ambit of another, or specific embodiments thereof, and vice versa.

Aspects of specific embodiments of this invention will be presented using specific examples and will be represented in different figures. For clarity and ease of description, each aspect includes only a few embodiments. Different embodiments from different aspects may be combined or practiced separately, to design a customized process depending upon application requirements. Many different combinations and sub-combinations of a few representative processes shown within the broad framework of this invention, that may be apparent to those skilled in the art but not explicitly shown or described, should not be construed as precluded.

Figure 1A:
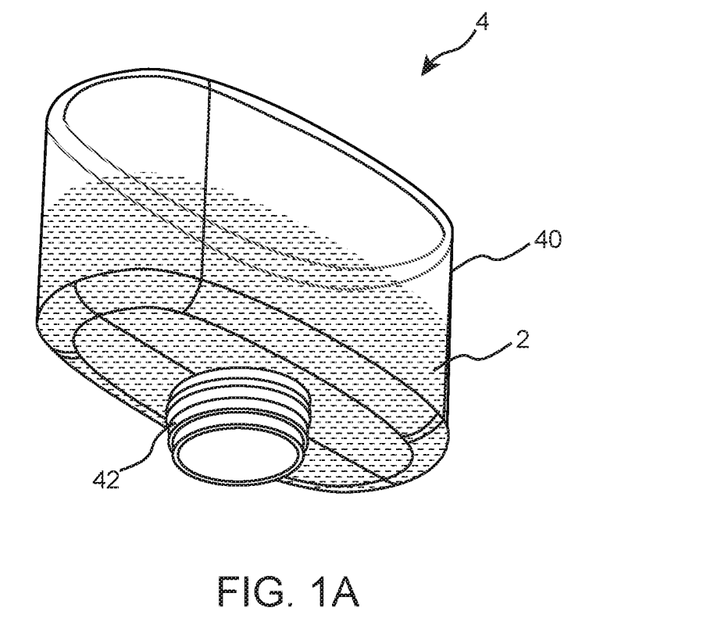
FIG. 1A illustrates a cartridge 4 in accordance with specific embodiments of the present invention.
Figure 1B:
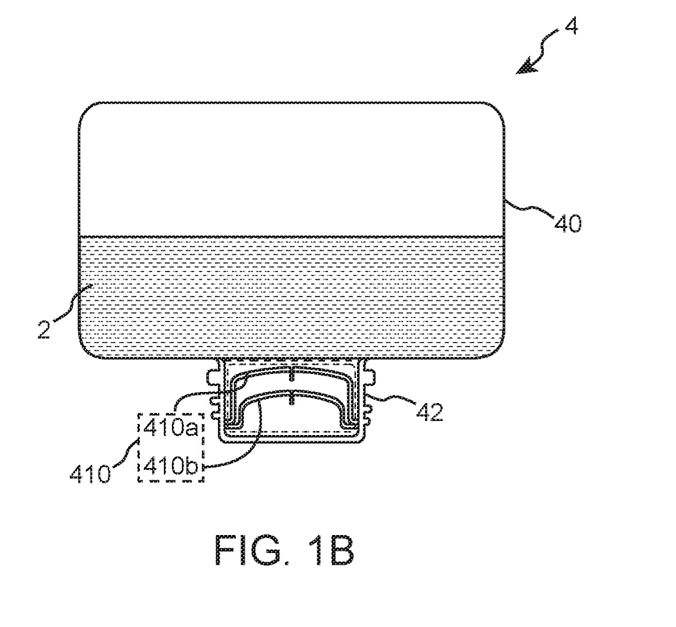
FIG. 1B illustrates a cross-sectional view of the cartridge 4 in accordance with specific embodiments of the present invention.

FIGS. 1A-1B show a cartridge 4 for use in an oral care appliance, wherein the cartridge 4 comprises a housing 40 for storing an oral care composition 2, e.g. dentifrice, and a connection interface 42 configured to form a detachable connection with a base unit of the oral care appliance. The cartridge 4 further comprises a valve assembly 410 configured to prevent escape of the oral care composition 2 when the connection interface 42 is in a detached position and to allow flow of the oral care composition 2 through the connection interface 42 to the oral care appliance when the connection interface 42 is in an attached position. The valve assembly 410 is positioned in the connection interface 42 of the cartridge 4 and comprises at least two valves 410a and 410b. Two valves greatly enhance the protection against leakage, especially during plugging and unplugging of the connection interface 42. More specifically, during the unplugging phase, the first valve 410a reaches the closed position while the second valve is still in the open position, the oral care composition 2 in the cartridge 4 is then prevented from leaking out even if the complete closing of the second valve 410b is not instantaneous. Furthermore, during the plugging phase, the second valve 410b is open while the first valve 410a remains closed. This first valve aperture forms a tight and sealed connection while the oral care composition 2 contained in the cartridge 40 is prevented from leaking by the closed valve 410a. The second valve 410a is then opened. The oral care composition 2 is allowed to flow only when both valves 410a and 410b are open. The valve assembly 410 thus provides a leak-proof connection of the connection interface 42 of the cartridge 4. Further, the valve assembly 410 ensures that the cartridge 4 can be easily attached or detached to the base unit of the oral care appliance without any leaks.

Figure 1C:
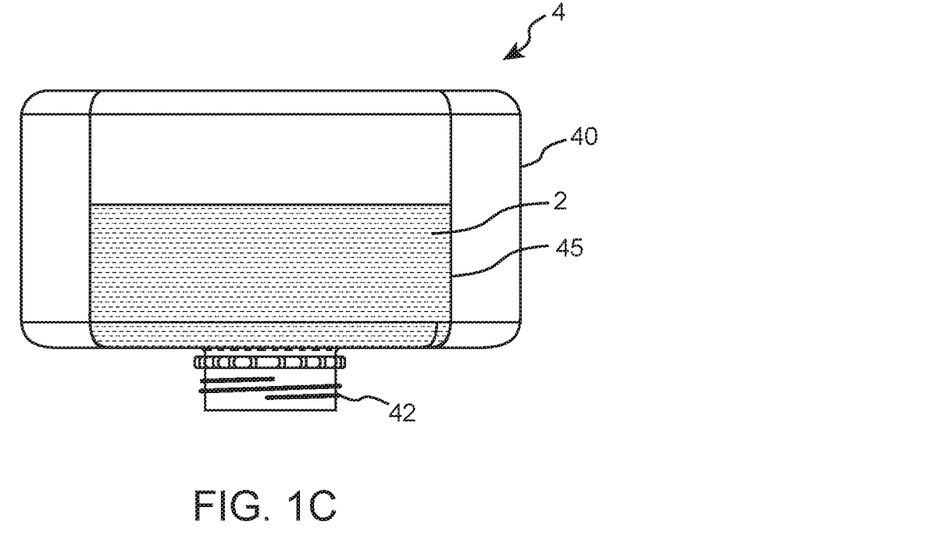
FIG. 1C illustrates a front view of the cartridge 4 comprising a cavity 45 in accordance with specific embodiments of the present invention.

In specific embodiments of the invention as shown in FIG. 1C, the housing 40 of the cartridge 4 comprises a cavity 45 for storing the oral care composition 2. Preferably, at least a portion of the housing 40 is rigid (i.e., is made up of a rigid material). In one example, the housing 40 is made up of hard material such as a material selected from, but not limited to, PET, plastic, Acrylonitrile butadiene styrene (ABS), PVC (polyvinyl chloride), a high-density polyethylene polymer or other such similar material known as a relatively hard material for oral care appliances to a person skilled in the art. Advantageously, the housing 40 of the cartridge 4 has a symmetrical shape to allow connection of the cartridge 4 to the base unit of the oral care appliance regardless of the direction of the cartridge 4. In one example, the shape of the housing 40 is selected from, but not limited to, circular, oval, rectangular, square, oblong or the like, when viewed from the top in a two-dimensional plane. In one specific example, the shape of the housing is oblong as shown in FIG. 1A. The shape of the housing 40 can be selected to fit the design of the oral care appliance or the base unit to facilitate the plugging of the cartridge 4.

In specific embodiments, the cartridge 4 is made of polyethylene terephthalate (PET) which is a thermoplastic plastic produced by polycondensation in the family of polyesters. This material is light weight, so it is ideal for shipping, chemically inert to prevent any chemical reaction with the oral care composition 2 and recyclable. The use of PET also presents a blow molding possibility enabling it to be manufactured into a cartridge.

In specific embodiments of the invention, the oral care composition 2 can be in solid, liquid, gaseous, gel or emulsion form or a combination thereof.

The oral composition referred to herein could comprise: a polishing agent such as an inert abrasive; a cleaning agent such as fluoride, activated charcoal, or a fluoride-free antibacterial composition; a halitosis treatment agent such as chlorine dioxide; or a whitening agent such as hydrogen peroxide. The active composition could also be any mixture of these kinds of agents and chemicals.

The dimensions of the cartridge 4 can be chosen so that its inner volume comprises between 100 to 400 ml of the oral care composition 2. In one example, length of the housing 40 can be in the range of 50 mm to 90 mm, width of the housing 40 can be in the range of 30 mm to 55 mm, and height of the housing can be in the range of 40 mm to 70 mm.

As mentioned above, the connection interface 42 of the cartridge 4 is configured to interact with the base unit. In other words, the connection interface 42 is configured to form a sealed connection with a corresponding connection interface of the base unit in order to allow the flow of oral care composition 2 from the cartridge 4. In order to do so, the valve assembly 410 comprises at least the two valve(s) 410a and 410b which can be made up of flexible material selected from, but not limited to, silicon, polymers, thermosetting silicone material, rubber, vinyl-methyl-silicone or any other flexible material for oral care appliances known to a person skilled in the art. As shown on the figures, the valve(s) 410a and 410b are configured in series to make a watertight sealing in the connection interface 42. Moreover, the valves 410a and 410b of the valve assembly 410 are configured to be opened/pierced while making the connection with corresponding members of the base unit in order to form at least one fluidic path allowing flow of the oral care composition 2 through the connection interface 42 of the cartridge 4. In one specific example, the valve assembly 410 is configured to interact with a needle assembly present in the base unit to form the fluidic path allowing flow of the oral care composition 2 from the cartridge 4 to the oral care appliance. The space between the two valve(s) 410a and 410b can be set such that the deformations of the two valve(s) 410a and 410b are independent when the cartridge 4 is in the attached position.

The valve assembly 410 is thus configured to seal the cartridge 4, thus preventing the leakage/escape of the oral care composition 2 when the cartridge 4 is not connected to the base unit (i.e., when the connection interface 42 is in the detached position).

Figure 1D:
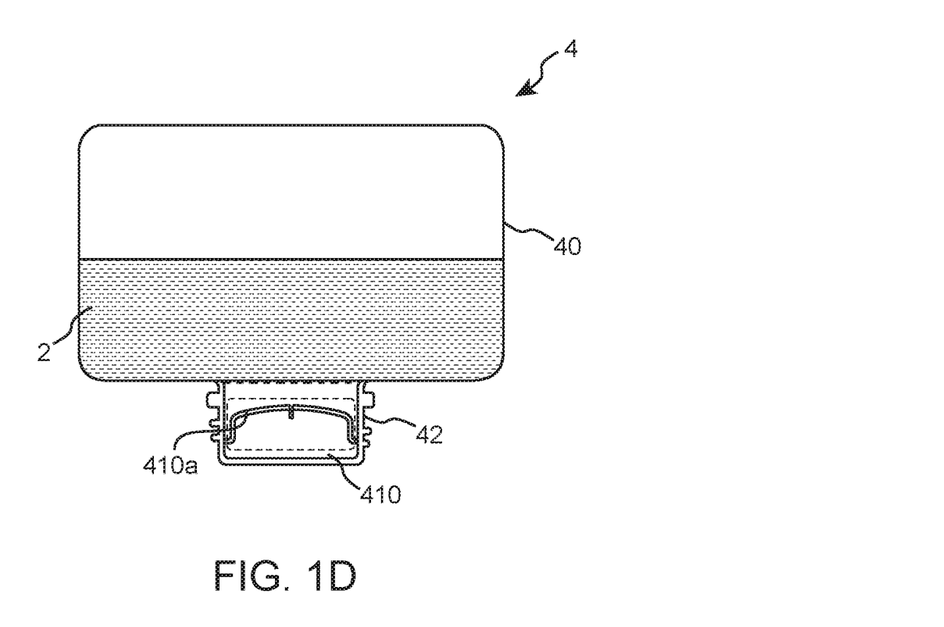
FIG. 1D illustrates a cross-sectional view of the cartridge 4 having one valve 410a in accordance with specific embodiments of the present invention.

In specific embodiments of the invention, the valve assembly 410 comprises only one valve 410a as shown in FIG. 1D to prevent escape of the oral care composition 2 when the connection interface 42 is in the detached position and to allow flow of the oral care composition 2 through the connection interface 42 to the oral care appliance when the connection interface 42 is in the attached position. In this case, the valve 410a is preferably thicker or made up of more rigid material as compared to the valve assembly 410 with at least two valves in order to ensure good sealing of the cartridge 4 when the connection interface 42 is in the detached position. Moreover, to ensure good sealing of the cartridge 4, the shape of the valve 410a can be selected from, but not limited to duck bill, umbrella, canopy or the like.

Figure 2A:
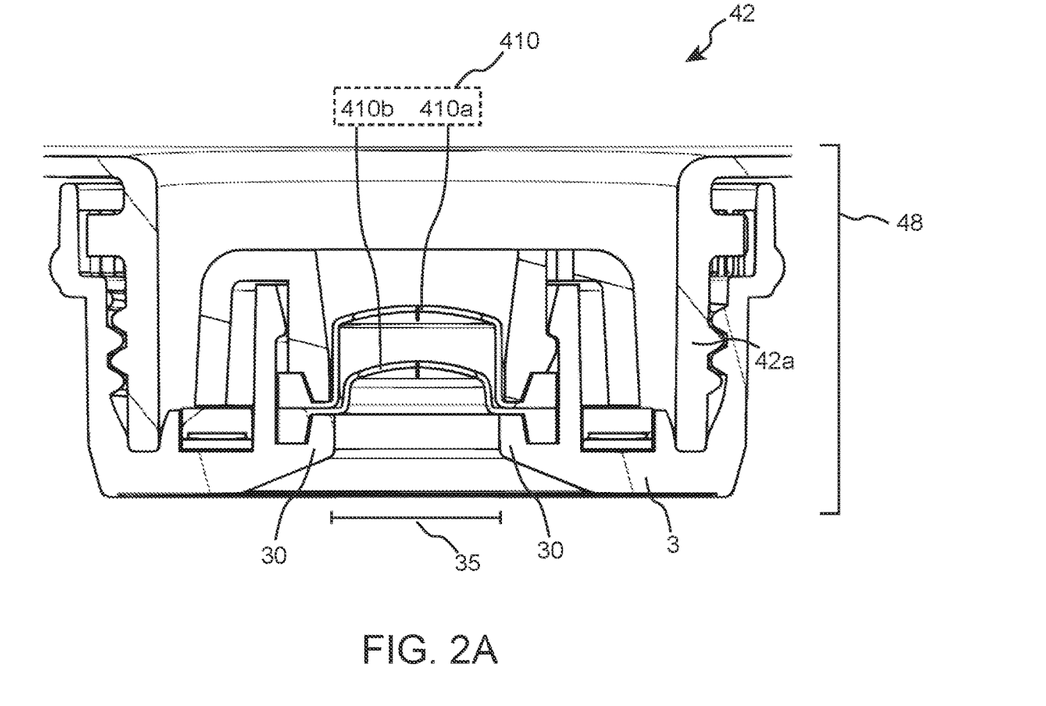
FIG. 2A illustrates a cross-sectional view of a connection interface 42 of the cartridge 4 in accordance with specific embodiments of the present invention.

In specific embodiments of the invention, the connection interface 42 is a cartridge neck 48 as shown in FIG. 2A. The cartridge neck 48 further comprises a cap 3 to provide a closure to the cartridge 4. The cap 3 can be coupled to the outer wall 42a of the connection interface 42 by a connection selected from, but not limited to, a snug fit connection, a key-lock connection, a threaded connection or the like. In one example, the connection between the cap 3 and the connection interface 42 is a threaded connection as shown in FIG. 2A. The cap 3 comprises a member 30 configured to hold the valve assembly 410 when the cap 3 is engaged with the cartridge neck 48. The member 30 can be a protruding member configured to hold the valve assembly 410 circumferentially. The shape of the member 30 can be selected to any suitable shape complementary to the shape of valve assembly 410 arranged in the cartridge 4 and/or to provide enough support to the valve assembly 410 when the cartridge 4 is in the attached position. The cap 3 further comprises a hole 35 configured to allow a needle assembly of the base unit to pass through it and interact with the valve assembly 410 of the cartridge 4. The diameter of the hole 35 is complementary to the diameter of the valve assembly 410 and diameter of the needle assembly. In one example, the diameter of the hole 35 is selected from 2 mm to 14 mm. The cap 3 is configured to have complementary dimensions in order to engage with the cartridge neck 48. In one example, the diameter of the cap 3 is complementary to the external diameter of the cartridge neck 48. The exterior diameter of the cap 3 may be in the range of 28 mm to 38 mm while the interior diameter of the cap 3 is slightly larger than the exterior diameter of the cartridge neck 48 to ensure tight connection between the cartridge neck 48 and the cap 3.

Figure 2B:
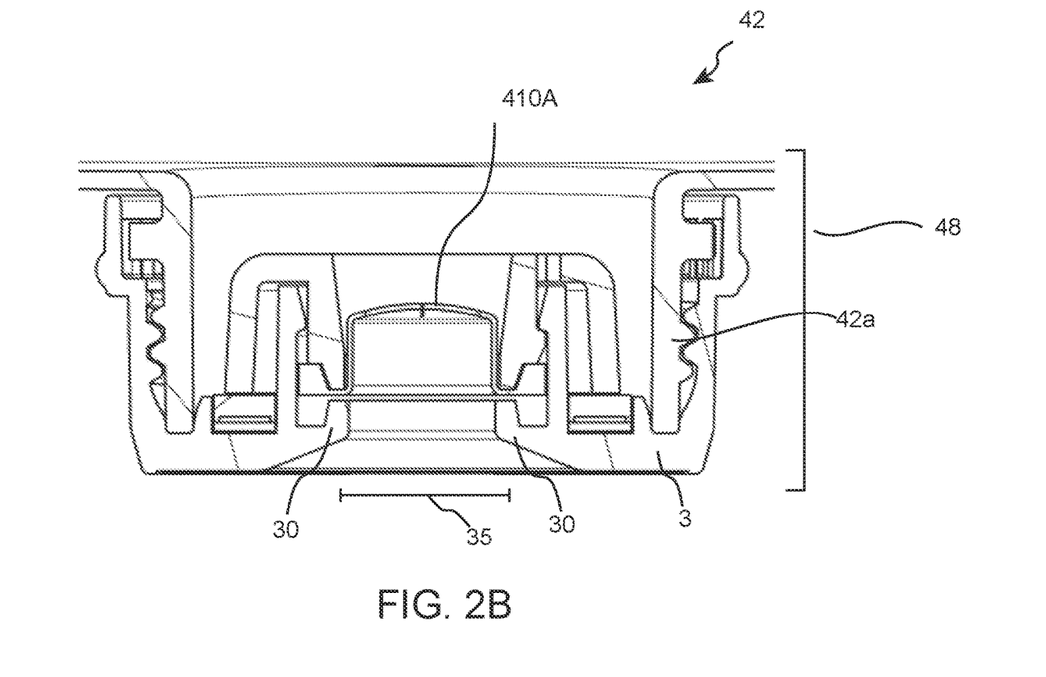
FIG. 2B illustrates a cross-sectional view of the connection interface 42 with only one valve 410a in accordance with specific embodiments of the present invention.

FIG. 2B illustrates a cross-sectional view of the connection interface 42 with only one valve 410a. In specific embodiments of the invention, the connection interface 42 is engaged to the cap 3 via outer wall 42a of the connection interface 42. The cap 3 comprises a member 30 configured to hold the valve assembly 410. The valve 410a of the valve assembly is configured to be opened/pierced while making the connection with corresponding members of the base unit to form at least one fluidic path allowing flow of the oral care composition 2 through the connection interface 42 of the cartridge 4.

Figure 3:
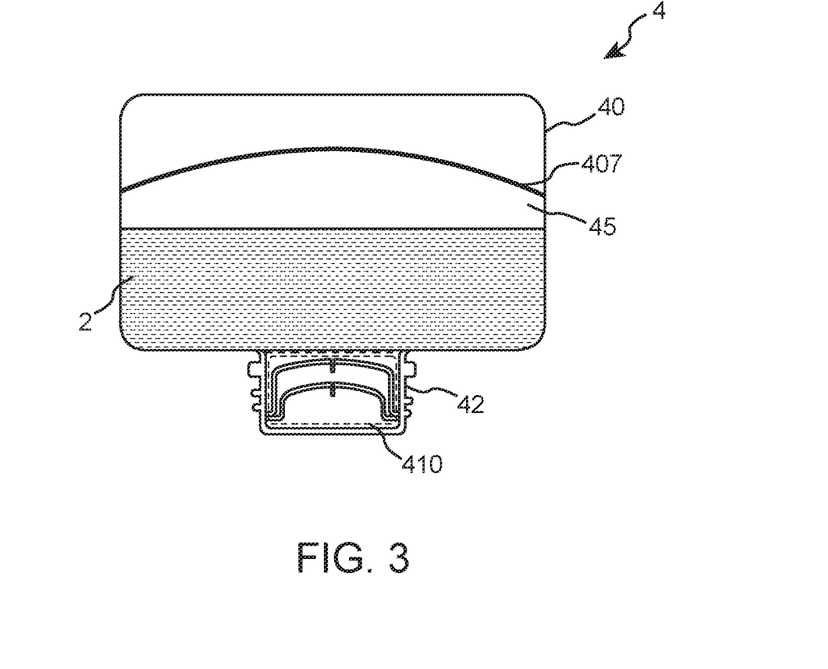
FIG. 3 illustrates the cartridge 4 comprising a flexible membrane 407 in accordance with specific embodiments of the present invention.

In specific embodiments of the invention as shown in FIG. 3, the housing 40 of the cartridge 4 comprises a flexible membrane 407 configured to deform in response to a pressure difference. The flexible membrane 407 forms the cavity 45 to store the oral care composition 2 and can be deformed to dispense the oral care composition 2 from the cartridge 4 under the effect of pressure. The flexible membrane 407 is made up of flexible material selected from, but not limited to, silicon, soft polymer or the like. In another embodiment of the invention, the oral care composition 2 can be dispensed out from cartridge 4 as shown in FIG. 3 with the help of a pump, thereby creating a negative pressure difference between the cavity 45 and the exterior environment, thus aspirating the oral care composition 2 into the base unit 6 or, alternatively, creating a positive pressure between the area above the flexible membrane 407 and the cavity 45, thus pushing the oral care composition 2 into the base unit 6.

Figure 4:
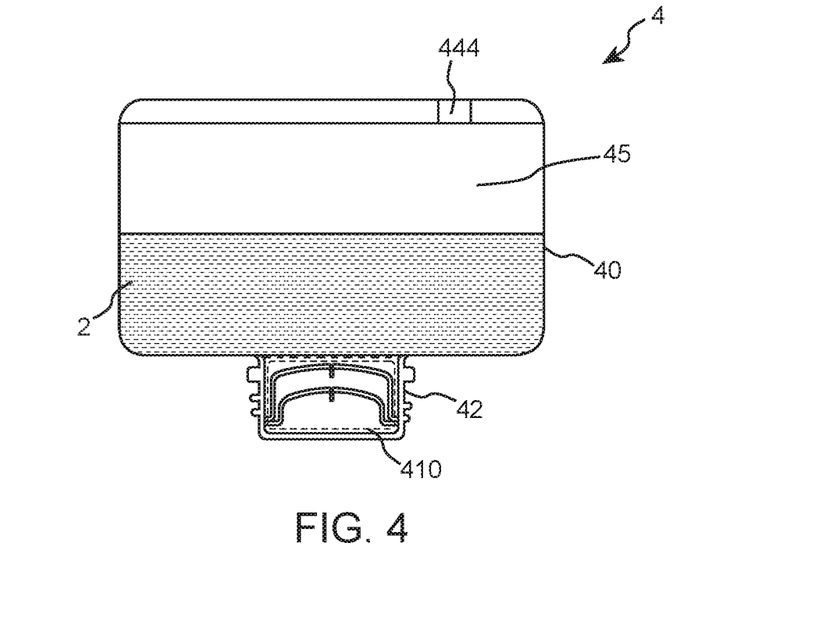
FIG. 4 illustrates the cartridge 4 comprising an air intake aperture 444 in accordance with specific embodiments of the present invention.

In specific embodiments of the invention as shown in FIG. 4, the cartridge 4 comprises an air intake aperture 444 present on the housing 40 itself. In another embodiment of the invention, the air intake aperture 444 is provided with a valve configured to regulate the inlet of air into the cartridge 4. In one example, the air intake aperture 444 can be provided for regulating the pressure inside the cartridge 4 and the valve on the air intake aperture 444 is provided to prevent the oral care composition 2 from leaking out of the cartridge 4 during transportation and handling. In other example, the valve permits insertion of air inside the cartridge 4 to equalize the pressure when the oral care composition 2 is aspirated or dispensed from the cartridge 4. In some further particular examples, the air intake aperture 444 and the valve can be placed on any position in the housing 40 of the cartridge 4.

Figure 5A:
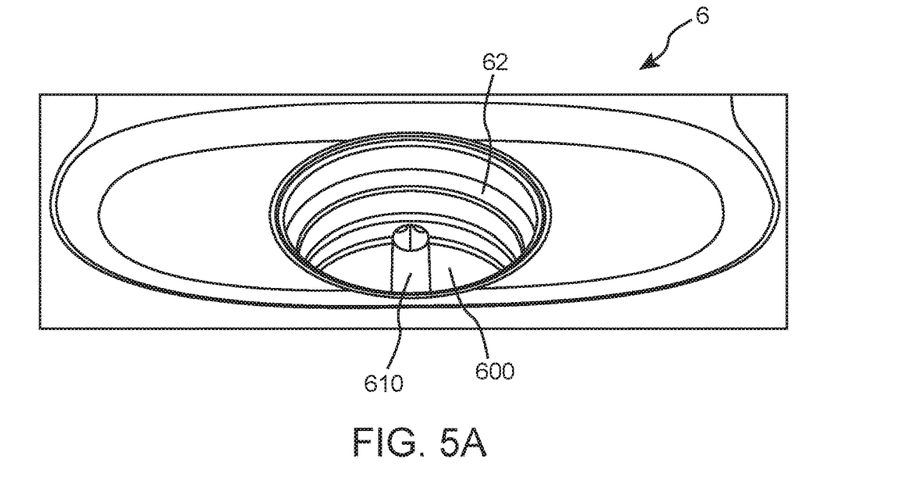
FIG. 5A illustrates a base unit 6 in accordance with specific embodiments of the present invention.

In FIG. 5A, a base unit 6 according to specific embodiments of the invention comprises a connection interface 62 to be plugged to the cartridge 4. The base unit 6 further comprises a needle assembly 610 configured to be operatively engaged to the cartridge 4 to facilitate flow of the oral care composition 2 from the cartridge 4 into the oral care appliance.

Figure 5B:
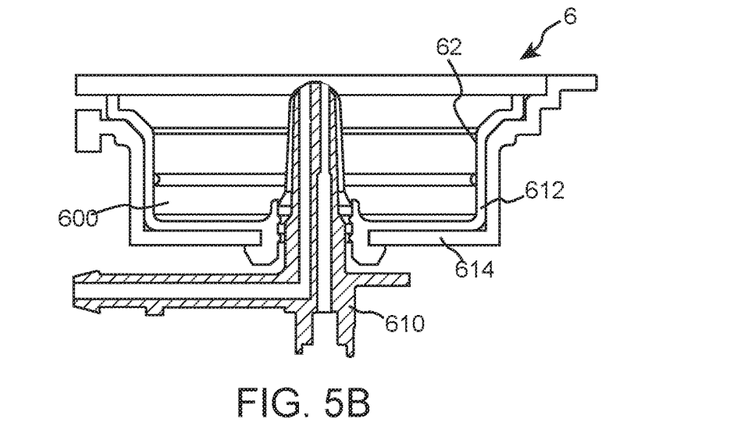
FIG. 5B illustrates a cross-sectional view of the base unit 6 in accordance with specific embodiments of the present invention.

As shown in FIG. 5B, the connection interface 62 of the base unit 6 comprises at least a first part 612 configured to make a connection with the corresponding connection interface 42 of the cartridge 4. The connection interface 62 further comprises at least a second part 614 configured to provide support to the connection between the cartridge 4 and the base unit 6. Materials of the first part 612 and the second part 614 can be chosen such that a snug fit connection can be formed between the cartridge 4 and the base unit 6 when the cartridge 4 is plugged to the base unit 6. As used herein, a snug fit refers to a clearance fit that is over line-to-line and can be released by hand. With reference to FIG. 5B, this refers to the fact that connection interface 62 may be partially compressed during connection to the cartridge. In specific examples, the first part 612 is made up of soft material selected from, but not limited to, TPU, silicone, TPE or other soft polymers used in oral appliances as known to persons skilled in the art. On the contrary, the second part 614 is preferably made up of hard material selected from, but not limited to, hard plastic, ABS, acrylic, nylon, PBT or other suitable hard materials used in oral care appliances as known to persons skilled in the art. Accordingly, the second part 614 provides support to the connection between the cartridge 4 and the base unit 6.

In specific embodiments of the invention, the connection interface 62 comprises means to form a snug fit connection with the cartridge 4. These means of the connection interface 62 further comprises at least a male connector or at least a female connector. In one example, the female connector 600 of the base unit 6 is configured to engage with the corresponding male connector of the cartridge 4. The connection between the female connector 600 and the corresponding male connector of the cartridge 4 can be a locking/keying connection, threaded connection, snug fit connection or the like.

In specific embodiments of the invention, the female connector 600 as shown in FIGS. 5A and 5B is configured to engage with the cartridge neck 48 of the cartridge 4.

In specific embodiments of the invention, the female connector 600 is engaged with the cartridge neck 48 by a rotation or sliding mechanism of the cartridge neck 48 against the female connector 600 of the base unit. According to another embodiment, the female connector 600 can be engaged with the cartridge neck 48 by a push-to-plug/push-to-release mechanism to ease the plugging of the cartridge 4.

In specific embodiments of the invention, diameter of the female connector 600 is only slightly larger than the exterior diameter of the cap 3 of the cartridge 4 to allow plugging and unplugging of the cartridge 4 without any leak.

Figure 6A:
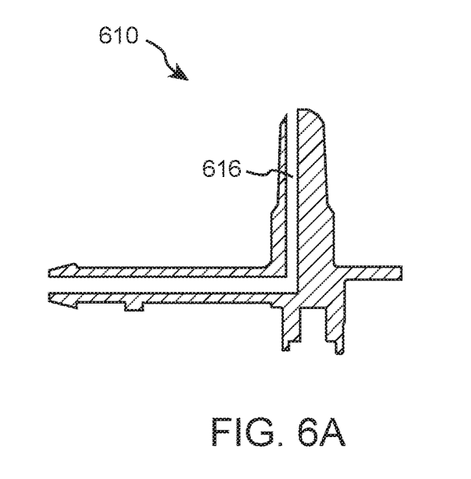
FIG. 6A illustrates a needle assembly 610 of the base unit 6 with one aperture 616 in accordance with specific embodiments of the present invention.
Figure 6B:
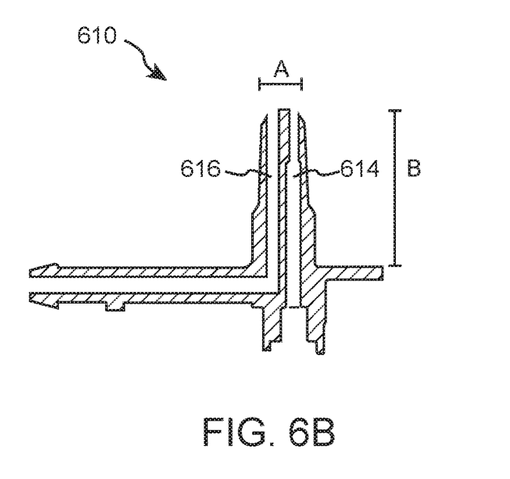
FIG. 6B illustrates a needle assembly 610 of the base unit 6 with at least two apertures 614 and 616 in accordance with specific embodiments of the present invention.

As mentioned above, the needle assembly 610 of the base unit 6 is configured to be operatively engaged to the cartridge 4. Accordingly, the needle assembly 610 is configured to interact with the valve assembly 410 of the cartridge 4, thereby forming at least a fluidic path to allow for the flow of the oral care composition 2 from the cartridge 4 into the oral care appliance. To do so, the needle assembly 610 is configured to have at least one aperture 616 configured to let the oral care composition 2 flow to the oral care appliance as shown in FIG. 6A. In specific embodiments of the invention, the needle assembly 610 comprises at least two apertures 614 and 616 as shown in FIG. 6B. The two apertures 614 and 616 facilitate the flow of the oral care composition 2 to the oral care appliance through the base unit 6 and the inlet of air into the cartridge 4. In one example, the apertures 614 and 616 can be of different dimensions, i.e. the smaller dimension aperture 614 acts as an air inlet (air intake aperture) to facilitate the inlet of air to the cartridge 4 and the larger dimension aperture 616 acts as an outlet for the oral care composition 2 from the cartridge 4. In another embodiment, the apertures 614 and 616 are of similar diameters.

The needle assembly 610 of the base unit 6 can be of any shape suitable for plugging into the cartridge 4. The shape of the needle assembly 610 may be selected from, but not limited to, cylindrical, conical, tubular or any suitable shape known to the person skilled in the art. The conical shape of the needle assembly 610 is shown in FIG. 6B.

In specific embodiments of the invention, the diameter of the aperture 614 is such that air flow is sufficient to balance the pressure inside the cartridge 4 around atmospheric pressure. For instance, the diameter can be between 0.5 to 3 mm.

In specific embodiments of the invention, the aperture 616 is dimensioned so that flow of the oral care composition 2 is not restrained, in other words, the pressure loss caused by the aperture 616 is limited to reach a suitable flow rate of the oral are composition 2 when the base unit 6 is plugged into the cartridge 4. For instance, the diameter of the aperture 616 can be between 0.5 to 4 mm. In specific embodiments of the invention, overall diameter of the needle assembly 610 is such that the assembly 610 is resistant enough to endure the life cycle of the oral care appliance. Furthermore, its conical shape ensures the good plugging/unplugging and a good sealing with the valve assembly 410. Preferably, the diameter of the needle assembly 610 is just a little bit smaller than aperture diameter of the valve assembly 410 to allow for numerous plugging/unplugging without damaging the valves 410a, 410b as well as to ensure good sealing between the exterior diameter of the needle assembly 610 and the valves assembly 410 when the base unit is plugged into the cartridge 4.

In specific embodiments of the invention, the length B of the needle assembly 610 is dimensioned so that the length is long enough to penetrate the valve assembly 410 positioned in the connection interface 42 of the cartridge 4 and short enough so that the apertures 614 and 616 are as low as possible in the cartridge 4 to allow for draining of the entire volume of the oral care composition 2 contained in the cartridge 4.

For instance, the diameter A of the needle assembly 610 can be between 3 to 15 mm and the length B of the needle assembly 610 can be between 10 to 30 mm.

Figure 7A:
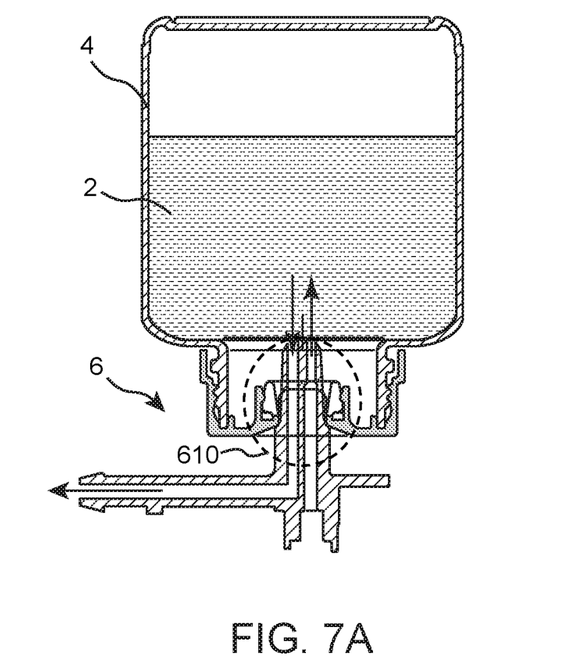
FIG. 7A shows the base unit 6 plugged into the cartridge 4 in accordance with specific embodiments of the present invention.

FIG. 7A shows the cartridge 4 plugged into the base unit 6 in specific embodiments of the invention. When the needle assembly 610 of the base unit 6 punctures the cartridge 4 and when the oral care composition 2 is dispensed from the cartridge 4 to the base unit 6, a pressure difference is generated between the interior of the cartridge 4 and the outside air. Due to the pressure difference, the air is injected inside the cartridge 4 through the aperture 614. In one example, the air injection can be done in a passive manner. The injected air equalizes the pressure when the oral care composition 2 is dispensed via the aperture 616 from the cartridge 4. The conical shape of the needle assembly 610 forces the two valves 410a and 410b to be in open position resulting in a plugging of the needle assembly 610 to the cartridge 4. The plugging of the needle assembly 610 to the cartridge 4 facilitates the flow of oral care composition 2 from the cartridge 4 to the oral care appliance.

Figure 7B:
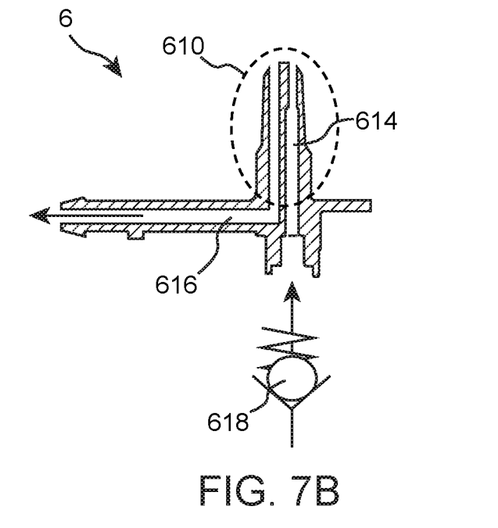
FIG. 7B illustrates the base unit 6 with a check valve 618 in accordance with specific embodiments of the present invention.

In specific embodiments of the invention in accordance with FIG. 7B, the air dispensed through the aperture 614 can be regulated by a check valve 618.

In specific embodiments of the invention, the check valve 618 prevents the oral care composition 2 from leaking through the aperture 614 when the cartridge 4 is plugged-in but not in use.

Figure 8:
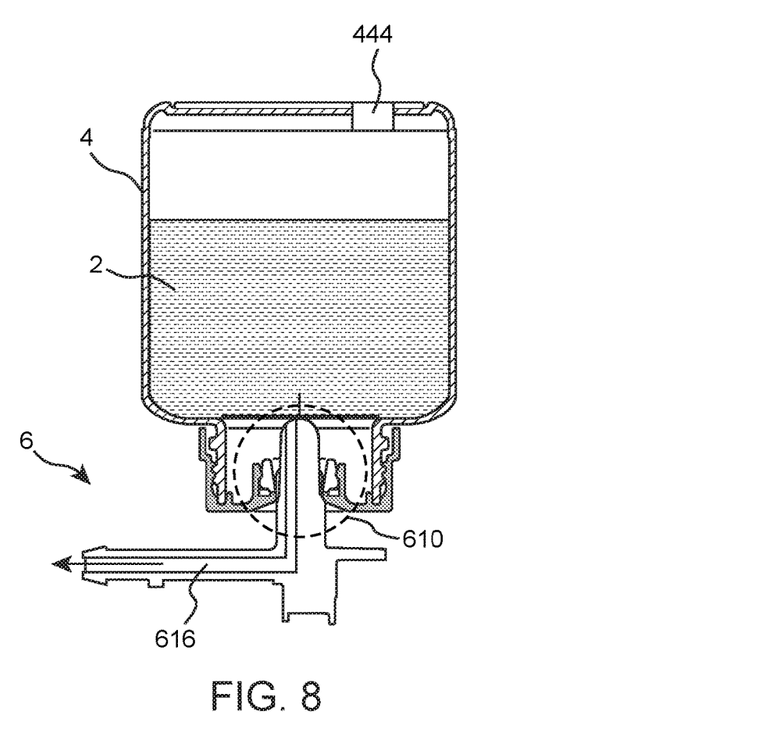
FIG. 8 illustrates the cartridge 4 with the air intake aperture 444 positioned on the base unit 6 in accordance with specific embodiments of the present invention.

FIG. 8 shows the base unit 6 plugged to the cartridge 4. In the illustrated example, the needle assembly 610 of the base unit 6 has a single aperture 616 to allow the dispensing of the oral care composition 2 from the cartridge 4. An air intake aperture 444 provided on top of the cartridge 4 permits insertion of air inside the cartridge 4 to equalize the pressure when the oral care composition 2 is dispensed from the cartridge 4 through the aperture 616 of the needle assembly 610. In specific embodiments of the invention, the air aperture 444 can also comprise a valve to regulate the air entering inside the cartridge 4.

Figure 9A:
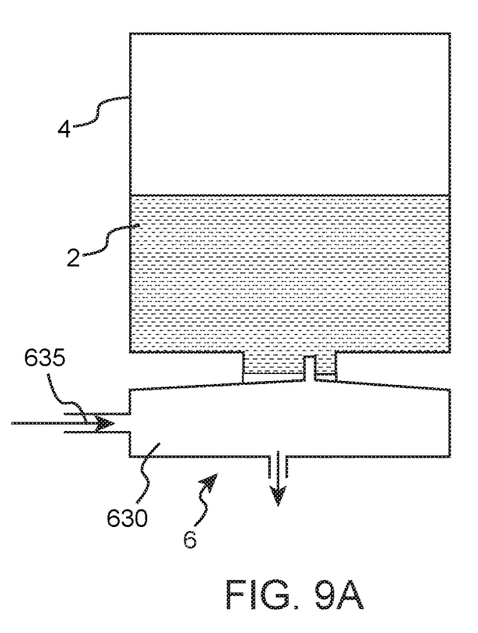
FIGS. 9A, 9B and 9C illustrate the base unit 6 comprising a mixing chamber 630 plugged to the cartridge 4 in accordance with specific embodiments of the present invention.
Figure 9B:
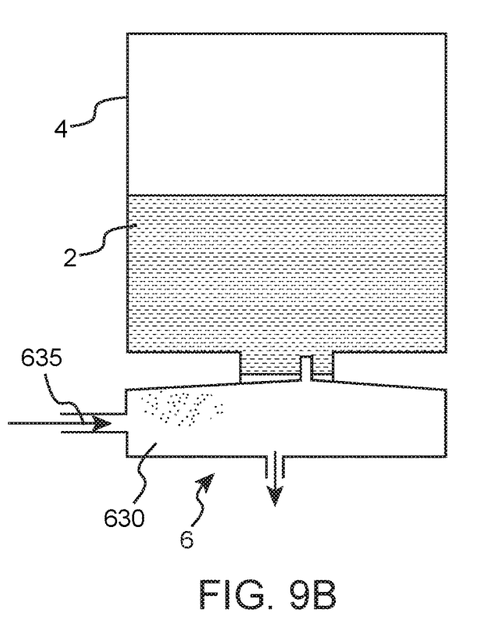
Figure 9C:
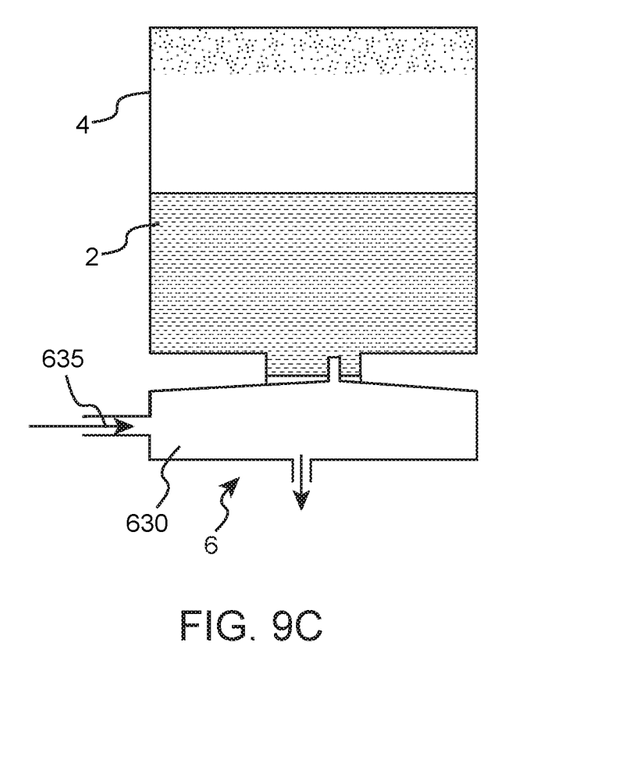

In specific embodiments of the invention as shown in FIG. 9A, the base unit 6 comprises a mixing chamber 630 having an air inlet 635. The mixing chamber 630 is configured to form a snug fit connection with the cartridge 4 when the cartridge 4 is plugged into the base unit 6. During the dispensing of the oral care composition 2 from the cartridge 4, air enters through the air inlet 635 which accumulates at the top of the mixing chamber 630 as shown in FIG. 9B. When the dispensing of the oral care composition 2 stops, the air accumulated in the mixing chamber 630 is transferred to the top of the cartridge 4 as shown in FIG. 9C due to difference of the density between the oral care composition 2 and the air.

During the aspiration/dispensing of the oral care composition 2 from the cartridge 4, a pressure difference is developed between the cartridge 4 and the outside air (e.g., in the mixing chamber 630). To equalize the pressure developed in the cartridge 4 and the outside of the cartridge 4, air is injected in the cartridge 4 through the air inlet aperture 635.

Figure 10:
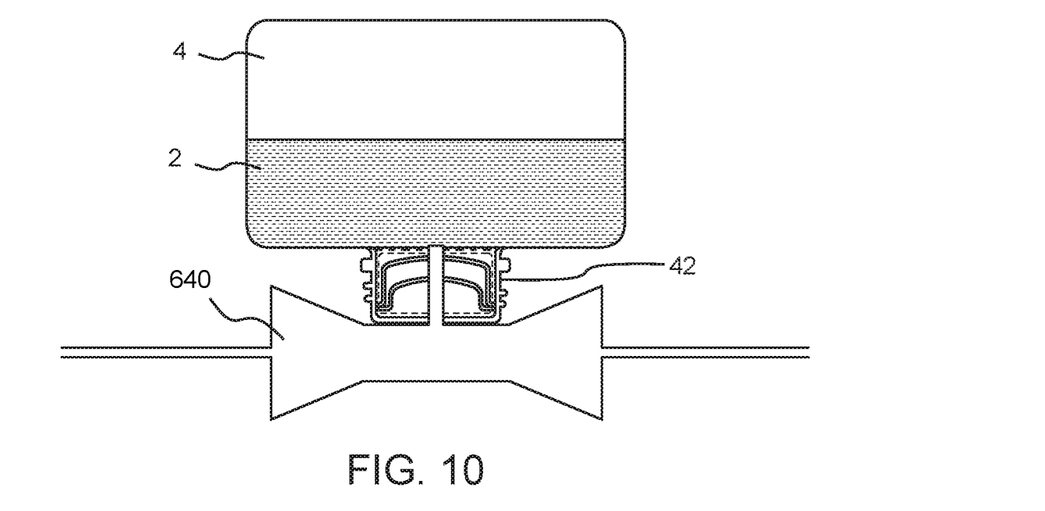
FIG. 10 illustrate the base unit 6 comprising a venturi effect chamber 640 plugged to the cartridge 4 in accordance with specific embodiments of the present invention.

In specific embodiments of the invention as shown in FIG. 10, the base unit 6 comprises a venturi effect chamber 640 to control flow rate of the oral care composition 2 from the cartridge 4. The venturi effect chamber 640 allows for dispensing of the oral care composition 2 in solid, liquid or gaseous phase. A neutral fluid can be circulated at high velocity into the chamber 640 and, due to venturi effect, a difference of pressure is created between the chamber 640 and the cartridge 4 which drives a certain amount of the oral care composition 2 into the chamber 640. The quantity of the oral care composition 2 is controlled by the dimensions of the outlet of the cartridge 4, the flow rate of the neutral fluid and the two flow properties. In one example, the volume of the oral care composition 2 is controlled by the diameter of the opening in the cartridge neck 48. In one embodiment, the neutral fluid is water.

In specific embodiments of the invention, a controlled quantity of the oral care composition 2 is aspirated from the cartridge 4. The aspiration can be done by a pump or any other aspiration means. A vacuum can be created in the base unit 6 with help of a pump to aspirate the oral care composition 2 through the needle assembly 610 to the oral care appliance.

In specific embodiments of the invention, the vacuum may be created in the base unit 6 using a vacuum pump, peristaltic pump, a tailor-made pump, or any one-way pump or two-way pumps.

Figure 11A:
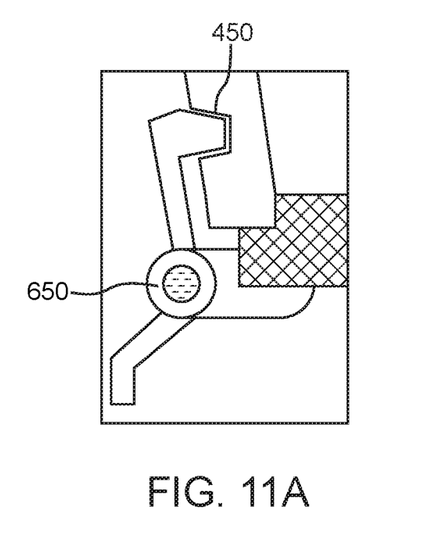
FIG. 11A illustrates a portion of a push to plug mechanism in accordance with specific embodiments of the present invention.
Figure 11B:
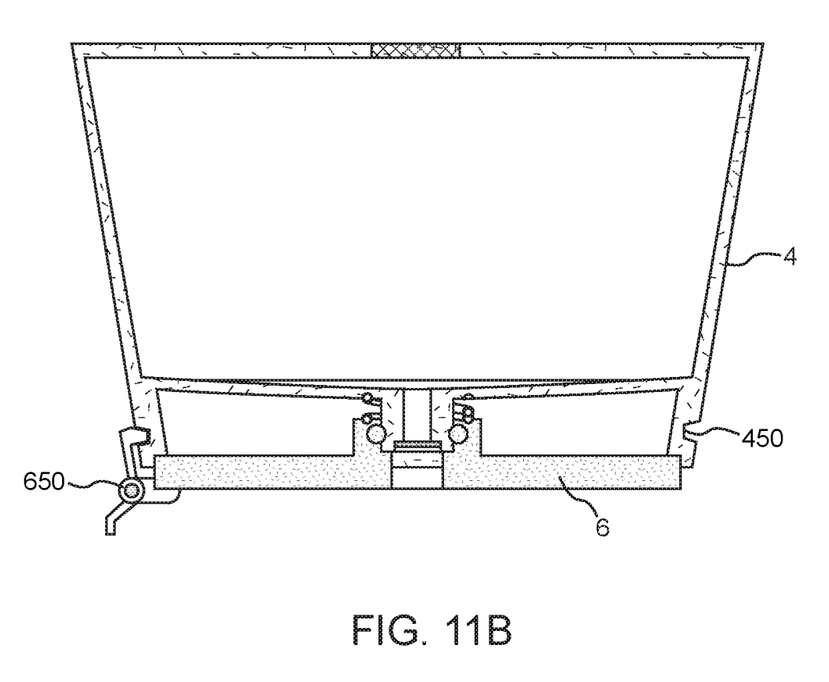
FIG. 11B illustrates the cartridge 4 and the base unit 6 coupled via a push to plug mechanism in accordance with specific embodiments of the present invention.

In specific embodiments of the invention, the connection between the cartridge 4 and the base unit 6 is secured by a push to plug connection as shown in FIG. 11A-11B. In such a case, the cartridge 4 is plugged into the base unit 6, wherein the base unit 6 comprises at least one spring member 650. The spring member 650 is configured to engage with a corresponding member 450 of the cartridge 4 to secure the connection when the cartridge 4 is plugged into the base unit 6. In order to release the cartridge 4 from the base unit 4, the spring member 650 is pushed downwards, thereby pushing the cartridge 4 upwards to facilitate it's unplugging from the base unit 6.

In specific embodiments of the invention, the valve assembly 410 is opened when a calibrated positive pressure difference between the cavity 45 and the connection between the valve assembly 410 and the base unit 6 is established.

This pressure difference might be generated by a pump or any means to generate a vacuum.

In specific embodiments of the invention, the cartridge 4 acts as a reservoir for storing the oral care composition 2. The reservoir is provided to be plugged once in the base unit 6 to provide the oral care composition 2. After utilizing the contained oral care composition 2 in the reservoir, the user can refill the reservoir with a fresh lot of oral care composition 2.

In specific embodiments of the invention, the cartridge 4 may be selected from, but not limited to, a partially or totally flexible container, a dentifrice tube, a sachet or other material or structure used to store and dispense a composition known to persons skilled in the art. In one example, the cartridge 4 is a disposable sachet with a cartridge neck 48 to be coupled to the base unit 6.

In specific embodiments of the invention, the oral care composition 2 can be stored in a small dose container and inserted anywhere in the oral care appliance, not requiring the cartridge 4 nor a reservoir.

Specific embodiments of the invention provide a cartridge that may be rigid and/or sealed to facilitate shipping and handling without damages/leaks. Moreover, the cartridge may be an economical disposable cartridge for use in the oral care appliance. Furthermore, the cartridge can be easily plugged to and unplugged from an oral care appliance without any leaks.

Although the invention has been described with regard to its embodiments, specific embodiments and various examples, it should be understood that various changes and modifications as would be obvious to one having the ordinary skill in this art may be made without departing from the scope of the invention as set forth in the claims appended hereto.

What is claimed is:

1. An oral care appliance comprising:
   a cartridge comprising: a housing for storing an oral care composition; a connection interface configured to form a detachable connection with the oral care appliance; and a valve assembly: (i) positioned in the connection interface; (ii) comprising at least two valves; and (iii) configured to prevent escape of the oral care composition when the connection interface is in a detached position and to allow flow of the oral care composition, through the at least two valves and the connection interface and to the oral care appliance, when the connection interface is in an attached position; and
   a base unit for use in the oral care appliance, comprising: a base connection interface to be plugged to the cartridge; and a needle assembly operatively engaged to the cartridge to facilitate flow of the oral care composition from the cartridge into the oral care appliance.

2. The oral care appliance of claim 1, wherein at least a portion of the housing is rigid.

3. The oral care appliance of claim 1, wherein the housing has a symmetrical shape.

4. The oral care appliance of claim 1, wherein the housing comprises a cavity for storing the oral care composition.

5. The oral care appliance of claim 1, wherein the housing comprises a flexible membrane configured to deform in response to pressure variations.

6. The oral care appliance of claim 1, wherein the at least two valves of the valve assembly are made of a flexible material.

7. The oral care appliance of claim 1, wherein the valve assembly forms at least one fluidic path allowing the flow of oral care composition through the connection interface when the connection interface is in the attached position.

8. The oral care appliance of claim 1, wherein the connection interface is a cartridge neck.

9. The oral care appliance of claim 1, wherein the cartridge further comprises an air intake aperture.

10. The oral care appliance of claim 1, wherein the needle assembly has at least one aperture.

11. The oral care appliance of claim 10, wherein the at least one aperture of the needle assembly is configured to let the oral care composition flow to the oral care appliance.

12. The oral care appliance of claim 11, wherein the needle assembly comprises an additional aperture to provide an inlet of air to the cartridge.

13. The oral care appliance of claim 1, wherein the needle assembly is configured to interact with the valve assembly.

14. The oral care appliance of claim 1, wherein the needle assembly is configured to form at least a fluidic path allowing the flow of oral care composition to the oral care appliance.

15. The oral care appliance of claim 1, further comprising at least a first part made up of soft material configured to ensure a snug fit connection between the cartridge and the base unit.

16. The oral care appliance of claim 15, further comprising at least a second part made up of hard material configured to provide support to the cartridge when the cartridge is plugged to the base unit.

17. The oral care appliance of claim 1, wherein the base unit is configured to allow plugging and unplugging of the cartridge to the oral care appliance without any leakage of the oral care composition.

18. The oral care appliance of claim 1, further comprising a means to form a snug fit connection with the cartridge.

19. The oral care appliance of claim 18, wherein the means comprises a male connector or a female connector.

* * * * *